United States Patent
Winther

(10) Patent No.: US 6,215,407 B1
(45) Date of Patent: Apr. 10, 2001

(54) HYDROCARBON DETECTION, ALERT, AND VAPOR REMOVAL SYSTEM WITH DISCHARGE CONTAINMENT CAPABILITIES

(76) Inventor: John Douglas Winther, 34552 Calle Paloma, Capistrand Beach, CA (US) 92624

( * ) Notice: Subject to any disclaimer, the term of this patent is extended or adjusted under 35 U.S.C. 154(b) by 0 days.

(21) Appl. No.: 09/590,601

(22) Filed: Jun. 9, 2000

(51) Int. Cl.[7] .................................................. G08B 17/10
(52) U.S. Cl. ........................ 340/632; 340/603; 340/984
(58) Field of Search .................................. 340/603, 605, 340/627, 632, 633, 634, 984

(56) References Cited

U.S. PATENT DOCUMENTS

| 4,256,985 | * | 3/1981 | Goodson et al. | 307/308 |
| 4,696,277 | * | 9/1987 | Katayama | 123/479 |
| 5,353,590 | * | 10/1994 | Pettit et al. | 60/274 |

* cited by examiner

*Primary Examiner*—Daniel J. Wu
(74) *Attorney, Agent, or Firm*—Michael I. Kroll

(57) ABSTRACT

The present invention 10 discloses a system for detecting and removing hydrocarbons from a vessel bilge area or the like comprised of one or more vaporous hydrocarbon sensor(s) 16 and one or more liquid submersible hydrocarbon sensor(s) 18. Each of the sensors has electrical connection to other members within the system for initiating a predetermined response to the presence of hydrocarbons 50. In the application of the system 10 within a vessel 12 bilge area 22, the vaporous hydrocarbon sensor(s) 16 would be located in an elevated portion of the bilge area having electrical connection to a forced air exhaust member 20 and audible and/or visual alarm members 26. The audible and/or visual alarm members 26 may incorporate existing lighting and audible elements within the vessel, such as, vessel running lights 40, 42 and horn 28. Further, the vaporous hydrocarbon sensor(s) 16 can be an integral part of the vessel ignition system. Incorporating vaporous hydrocarbon sensor(s) 16 and powered ventilation system within the ignition system 20 forms a failsafe system whereby, should an operator engage the ignition system while volatile vapors are present, the vaporous hydrocarbon sensor(s) 16 will engage the powered ventilation system 20 for a predetermined time period before energizing the engine 38. Further, the vaporous hydrocarbon sensor 16 would engage audio and/or visual warning members 26 should the sensor detect volatile vapors exceeding sensor parameters while the engine is running. In addition to the vaporous hydrocarbon sensor(s) 16, a liquid submersible hydrocarbon sensor 18 would be located in the bilge area 22 having electrical connection to the bilge pump 14 and audible and/or visual alarm members 26 for the purpose of automatically shutting down the bilge pump should the sensor detect emulsified hydrocarbons within the bilge water. Furthermore, the bilge pump shutdown alarms can be distinctly different from the vaporous hydrocarbon sensor alarms. An alternate embodiment is disclosed in which the present invention 10 is applied to a pipe 72 containing hydrocarbons.

15 Claims, 7 Drawing Sheets

HYDROCARBON DETECTION, ALERT, AND VAPOR REMOVAL SYSTEM WITH DISCHARGE CONTAINMENT CAPABILITIES

BACKGROUND OF THE INVENTION

1. Field of the Invention

The present invention relates generally to pollutant detection systems and, more specifically, to a system for detecting the presence of hydrocarbons in a bilge or pipe system and alerting the appropriate operator or monitor using audible and/or visual alarms while automatically shutting off the flow of contamination into the environment.

The system is comprised of one or more vaporous hydrocarbon sensor(s) and one or more liquid submersible hydrocarbon sensor(s). Each of the sensors having electrical connection to other members within the system for initiating a predetermined response to the presence of hydrocarbons.

In the application of the system within a vessel bilge area, the vaporous hydrocarbon sensor(s) would be located in an elevated portion of the bilge area having electrical connection to a forced air exhaust member and audible and/or visual alarm members. Said audible and/or visual alarm members may incorporate existing lighting and audible elements within the vessel, such as, vessel running lights and horn.

Further, the vaporous hydrocarbon sensor(s) can be an integral part of the vessel ignition system. While it is federally mandated that each compartment in a boat built after 1980 having a permanently installed gasoline engine with a cranking motor for remote starting have a powered ventilation system, there is no mandate for purging said system prior to engaging said engine. It recommended that the operator of the vessel check the bilge area for fuel and vapor contamination prior to vessel use. While this is prudent advice and is an element of an experienced vessel operator checklist for sea worthiness when moored, it is easily overlooked on the open water especially by the novice. Incorporating vaporous hydrocarbon sensor(s) and powered ventilation system within the ignition system forms a failsafe system whereby, should an operator engage the ignition system while volatile vapors are present, the vaporous hydrocarbon sensor(s) will engage the powered ventilation system for a predetermined time period before energizing the engine.

Further, the vaporous hydrocarbon sensor would engage audio and/or visual warning members should the sensor detect volatile vapors exceeding sensor parameters while the engine is running.

In addition to the vaporous hydrocarbon sensor(s), a liquid submersible hydrocarbon sensor would be located in the bilge area having electrical connection to the bilge pump and audible and/or visual alarm members for the purpose of automatically shutting down the bilge pump should the sensor detect emulsified hydrocarbons within the bilge water.

Furthermore, the bilge pump shutdown alarms can be distinctly different from the vaporous hydrocarbon sensor alarms.

2. Description of the Prior Art

There are other pollutant monitoring devices designed for detecting the presence of pollutants. Typical of these is U.S. Pat. No. 5,277,797 issued to Thomas S. Hargest on Jan. 11, 1994.

Another patent was issued to Douglas R. Hamburg et al. on Apr. 18, 1995 as U.S. Pat. No. 5,408,215. Yet another U.S. Pat. No. 5,467,643 was issued to Michael L. Barnett on Nov. 21, 1995.

U.S. Pat. No. 5,277,797

Inventor: Thomas S. Hargest

Issued: Jan. 11, 1994

An oil and water separator for separating oil from water collected in a bilge of a boat prior to discharging the water overboard. A reservoir is provided for receiving the mixture of oil and water from the bilge. The oil separates from the water and floats on top of the water. When only water is between a pair of spaced electrical probes carried in the reservoir, such causes a drain valve to be opened to drain the water from the reservoir. As the water is drained from the reservoir, the oil floating on top of the water will come between the probes and close the valve, stopping the draining of the water from the bottom of the reservoir. A mixture of oil and water is pumped from the tank carried in the bilge at an intermittent rate so that the mixture is allowed sufficient time to separate in the reservoir.

U.S. Pat. No. 5,408,215

Inventor: Douglas R. Hamburg

Issued: Apr. 18, 1995

An on-board monitoring system for an automotive emission catalyst has (I) a test chamber remote from the automobile's engine exhaust gas stream; (ii) apparatus for supplying the chamber with sampled exhaust gases sequestered from said stream; (iii) a single hydrocarbon sensor exposed to the exhaust gas in the chamber to render the signal responsive to the concentration of hydrocarbon in the chamber; and (iv) apparatus for comparing the sensed signal with a reference signal, and, if a predetermined distance is exceeded, the catalyst is indicated as faulty. Apparatus (ii) has a supply channel interconnected between the chamber and the gas stream upstream of the catalytic converter, a supply channel independently interconnected between the chamber and the gas stream downstream of the catalytic converter, and valve apparatus for permitting flow-through of no more than one channel to said chamber at any one moment, preferably cycled at a certain frequency. Method steps carried out by the System comprise: (a) periodically transferring a sample quantity of gas from the stream into a test chamber at a predetermined flow rate; (b) exposing a hydrocarbon sensor to the sequestered gas to generate a signal in proportion to the hydrocarbon in such gas; and (c) comparing the signal with a reference signal to determine if a predetermined difference exists and thereby conclude the catalyst is sufficiently degraded.

U.S. Pat. No. 5,467,643

Inventor: Michael L. Barnett

Issued: Nov. 21, 1995

A new method and apparatus for monitoring cooling water flow in a marine engine cooling water system to determine the functional status, and efficiency, of a marine engine cooling system and also monitoring bilge water flow in a bilge water pumping system to determine the functional status, and efficiency, of the bilge water pumping system.

While these pollutant detection systems may be suitable for the purposes for which they were designed, they would not be as suitable for the purposes of the present invention, as hereinafter described.

SUMMARY OF THE PRESENT INVENTION

The present invention discloses a system for detecting and removing hydrocarbons from a vessel bilge area or the like comprised of one or more vaporous hydrocarbon sensor(s) and one or more liquid submersible hydrocarbon sensor(s). Each of the sensors has electrical connection to other members within the system for initiating a predetermined response to the presence of hydrocarbons. In the application of the system within a vessel bilge area, the vaporous hydrocarbon sensor(s) would be located in an elevated portion of the bilge area having electrical connection to a forced air exhaust member and audible and/or visual alarm members. The audible and/or visual alarm members may incorporate existing lighting and audible elements within the vessel, such as, vessel running lights and horn. Further, the vaporous hydrocarbon sensor(s) can be an integral part of the vessel ignition system. Incorporating vaporous hydrocarbon sensor(s) and powered ventilation system within the ignition system forms a failsafe system whereby, should an operator engage the ignition system while volatile vapors are present, the vaporous hydrocarbon sensor(s) will engage the powered ventilation system for a predetermined time period before energizing the engine. Further, the vaporous hydrocarbon sensors would engage audio and/or visual warning members should the sensor detect volatile vapors exceeding sensor parameters while the engine is running. In addition to the vaporous hydrocarbon sensor(s), a liquid submersible hydrocarbon sensor would be located in the bilge area having electrical connection to the bilge pump and audible and/or visual alarm members for the purpose of automatically shutting down the bilge pump should the sensor detect emulsified hydrocarbons within the bilge water. Furthermore, the bilge pump shutdown alarms can be distinctly different from the vaporous hydrocarbon sensor alarms. An alternate embodiment is disclosed in which the present invention is applied to a pipe containing hydrocarbons.

A primary object of the present invention is to provide vessels with a hydrocarbon detection system.

Another object of the present invention is to provide a vessels bilge with one or more vaporous hydrocarbon sensors.

Yet another object of the present invention is to provide a vessel bilge with one or more vaporous hydrocarbon sensors that will automatically energize a power ventilation system upon detection of vaporous hydrocarbons.

Still yet another object of the present invention is to provide a vessel bilge with one or more vaporous hydrocarbon sensors that will automatically energize audio and/or visual alarms upon detection of vaporous hydrocarbons.

A further object of the present invention is to provide a vessel with an ignition system having one or more vaporous hydrocarbon sensors that will automatically energize a power ventilation system upon detection of vaporous hydrocarbons before energizing the engine.

A yet further object of the present invention is to provide a vessels bilge with one or more liquid submersible hydrocarbon sensors.

Another object of the present invention is to provide a vessel bilge with one or more liquid submersible hydrocarbon sensors that will automatically shut down the bilge pump upon detection of emulsified hydrocarbons.

Yet another object of the present invention is to provide a vessel bilge with one or more liquid submersible hydrocarbon sensors that will automatically energize audio and/or visual alarms upon detection of emulsified hydrocarbons.

Still yet another object of the present invention is to provide a vessel with an override mechanism that will energize the bilge pump regardless of detection of emulsified hydrocarbons.

A further object of the present invention is to provide a vessel with audio and/or visual alarms whereby the occupants of said vessel would be notified of hazardous accumulations of hydrocarbons within the vessel bilge.

A yet further object of the present invention is to provide a vessel with a forced air ventilation system having at least one vaporous hydrocarbon sensor that automatically energizes said ventilation system upon detection of hydrocarbons.

Another object of the present invention is to provide a hydrocarbon detection, alert, and vapor removal system for a vessels bilge utilizing the vessels running lights and horns to provide the visual and audible alarms to alert the crew to a potentially hazardous, toxic condition.

Yet another object of the present invention is to provide hydrocarbon detection, alert, and vapor removal system for a vessel bilge having an anti-theft feature that when activated disables the vessel A further object of the present invention is to provide a hydrocarbon detection and alert system for drain pipes expelling waste fluids into environmentally sensitive areas such as storm drains, sewage treatment run-off, commercial effluvium, etc., wherein an elevated level of hydrocarbons is detected by a sensor and closes the point of egress through which the contaminated fluid is being expelled into the environment until the toxic condition can be appropriately resolved. The hydrocarbon sensor immediately alerts a central office monitor of the business or agency responsible for maintaining the drainage system of the location of the toxic condition.

Additional objects of the present invention will appear as the description proceeds.

The present invention overcomes the shortcomings of the prior art by providing a hydrocarbon detection, alert, and vapor removal system wherein hydrocarbon sensor(s) monitors air and water accumulated in a bilge for the presence of hydrocarbons and upon detection notifies crew and passengers by flashing the vessels running lights and activating horns while shutting down the bilge pump to contain the contaminated water within the bilge and enabling a blower exhaust system to remove any volatile vapors from the contained area.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which.

LIST OF REFERENCE NUMERALS

Figure 1:
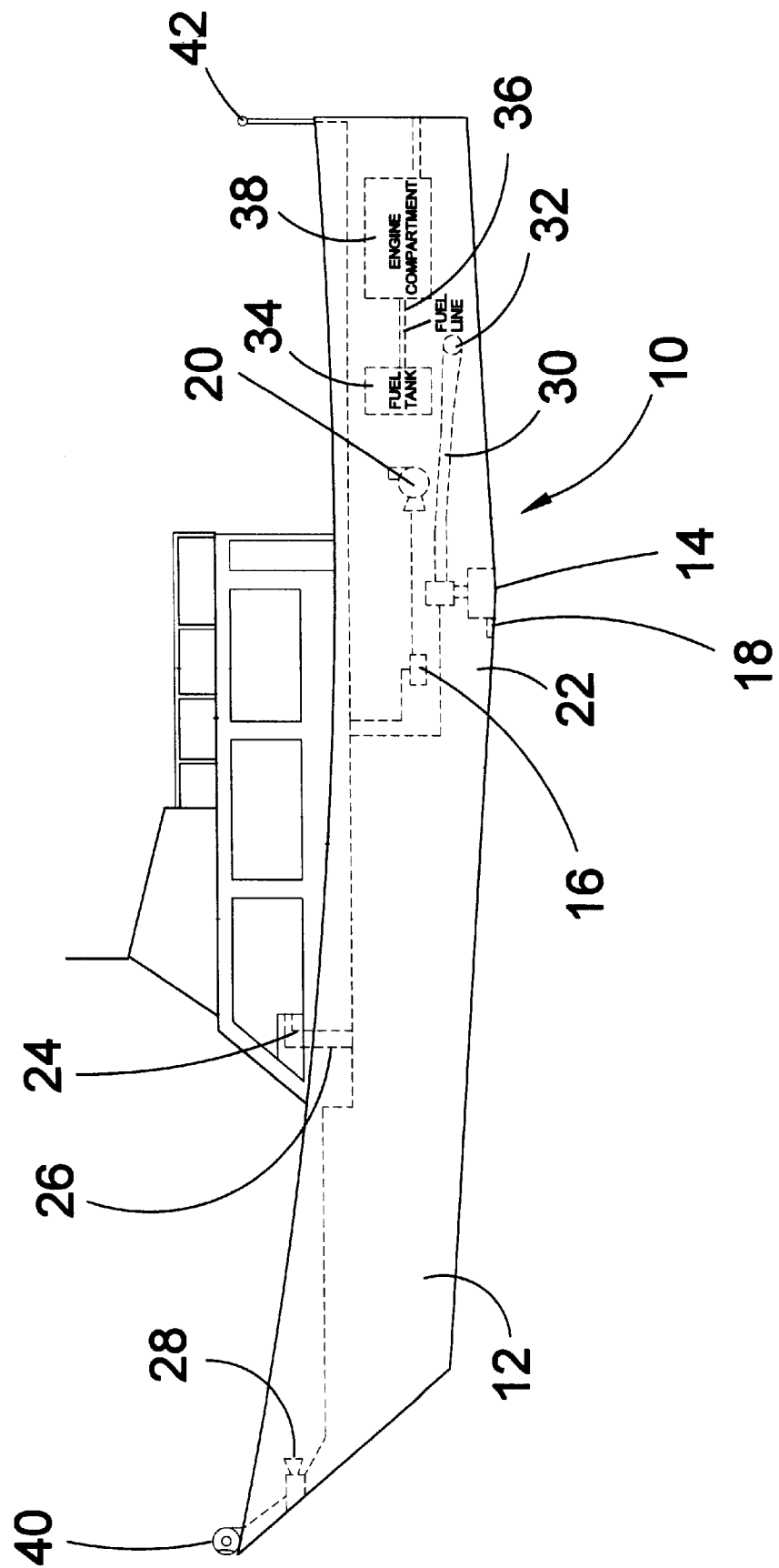
FIG. 1 is a side view of a vessel equipped with the present invention, which is inactive during normal operating conditions. Shown is a bilge area containing a bilge pump with a hydrocarbon sensor and a blower exhaust ventilator. Under normal operating conditions water taken on by the vessel accumulates in the bilge and is pumped outside of the vessel by the bilge pump as long as the hydrocarbon sensor is getting a negative reading.

With regard to reference numerals used, the following numbering is used throughout the drawings.

| 10 | present invention |
| 12 | vessel |
| 14 | bilge pump |
| 16 | vaporous hydrocarbon sensor |
| 18 | emulsion hydrocarbon sensor |
| 20 | exhaust blower |
| 22 | bilge area |
| 24 | optional security system |
| 26 | bilge alarm |
| 28 | horn |
| 30 | discharge line |
| 32 | discharge port |
| 34 | fuel tank |
| 36 | fuel line |
| 38 | engine compartment |
| 40 | bow lights |
| 42 | aft lights |
| 44 | flashers |
| 46 | bilge pump intake |
| 48 | external water body |
| 50 | fuel or oil leak |
| 52 | direction arrow |
| 54 | vapors |
| 56 | atmosphere |
| 58 | power supply |
| 60 | run off |
| 62 | roadway |
| 64 | storm drain |
| 66 | pipe system |
| 68 | holding resevoir |
| 70 | shutdown gate |
| 72 | discharge pipe |
| 74 | hydrocarbon sensor |
| 76 | discharge |
| 78 | pond or ocean |
| 80 | alarm monitor |
| 82 | shutdown sensor |

DESCRIPTION OF THE PREFERRED EMBODIMENT(S)

In order that the invention may be more fully understood, it will now be described, by way of example, with reference to the accompanying drawings in which FIGS. 1 through 7 illustrate the present invention being a hydrocarbon detection and removal system.

Turning to FIG. 1, shown therein is a side view of a vessel 12 equipped with the present invention 10, which is inactive during normal operating conditions. Shown is a bilge area 22 containing a bilge pump 14 with a vaporous 16 and emulsion 18 hydrocarbon sensor and a blower exhaust ventilator 20. Under normal operating conditions water taken on by the vessel 12 accumulates in the bilge 22 and is pumped outside of the vessel by the bilge pump 14 as long as the hydrocarbon sensor 18 is getting a negative reading. Also shown are an optional security system 24, a bilge alarm 26 and horn 28. Also shown are the discharge line 30 and port 32, fuel tank 34, fuel line 36, engine 38, bow lights 40, and aft lights 42.

Figure 2:
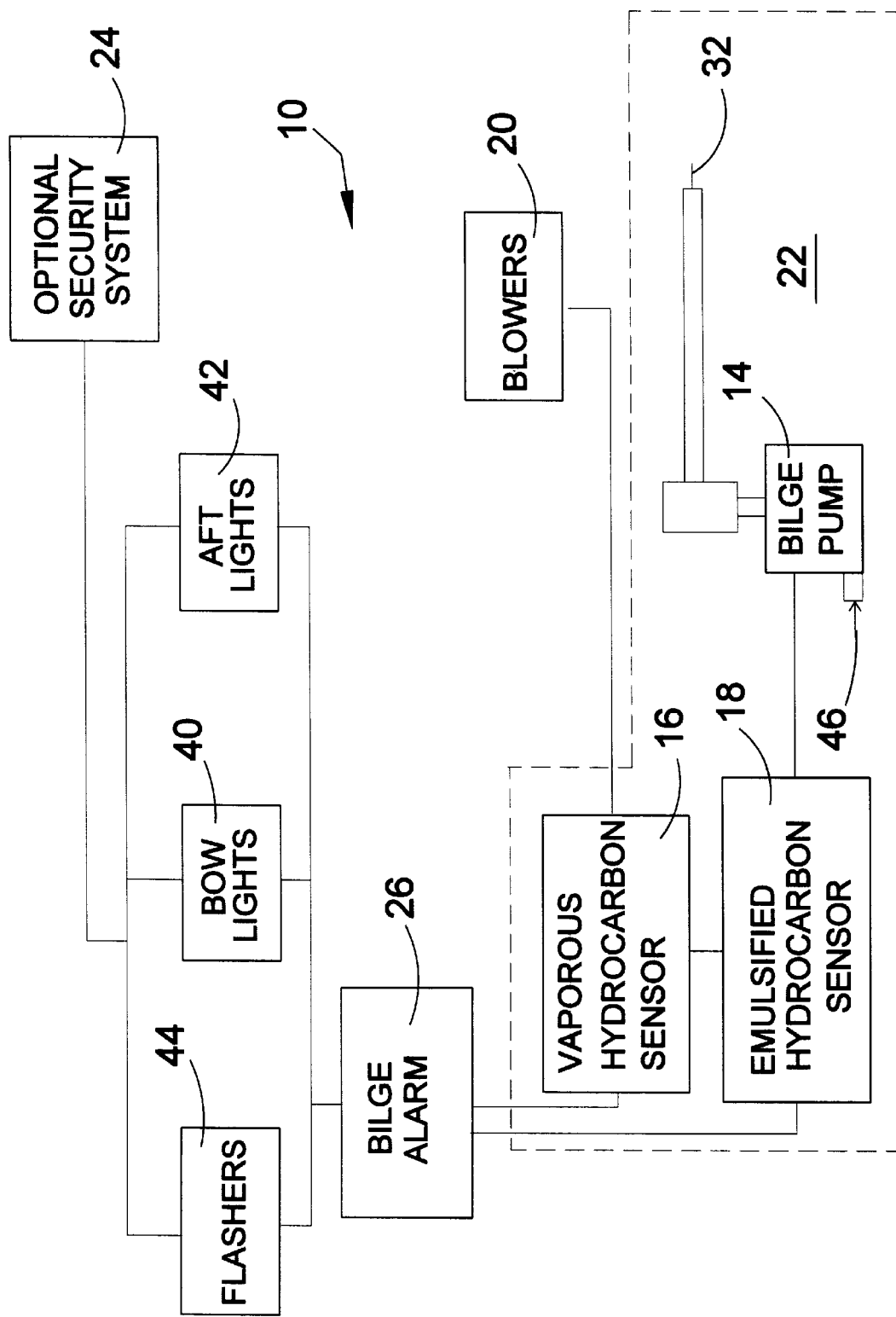
FIG. 2 is a block diagram of the present invention illustrating the interrelationship between the various components of the present invention.

Turning to FIG. 2, shown therein is a block diagram of the present invention 10 illustrating the interrelationship between the various components of the present invention showing the elements previously disclosed along with flashers 44 and bilge pump intake 46.

Figure 3:
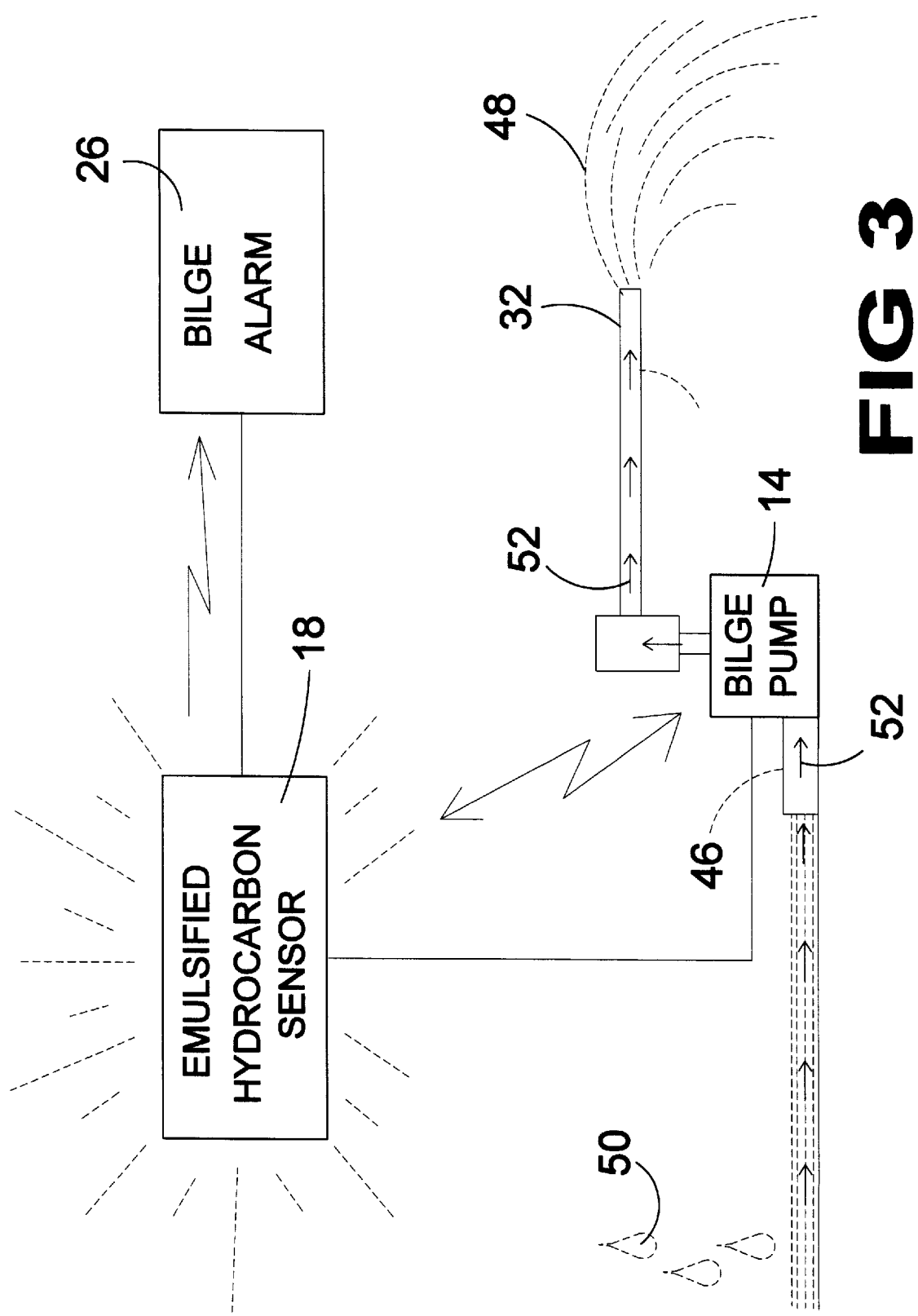
FIG. 3 is a diagrammatic view of the present invention in use demonstrating the flow of contaminated fluid through the bilge as it activates the hydrocarbon sensor and shuts down operation of the bilge pump thereby reducing or preventing contamination from being dumped through the discharge port and into the external body of water.

Turning to FIG. 3, shown therein is a diagrammatic view of the present invention in use demonstrating the flow of contaminated fluid 50 through the bilge as it activates the hydrocarbon sensor 18 and shuts down operation of the bilge pump 14 thereby reducing or preventing contamination from being dumped through the discharge port 32 and into the external body of water 48. Direction arrows 52 indicate the fluid flow.

Figure 4:
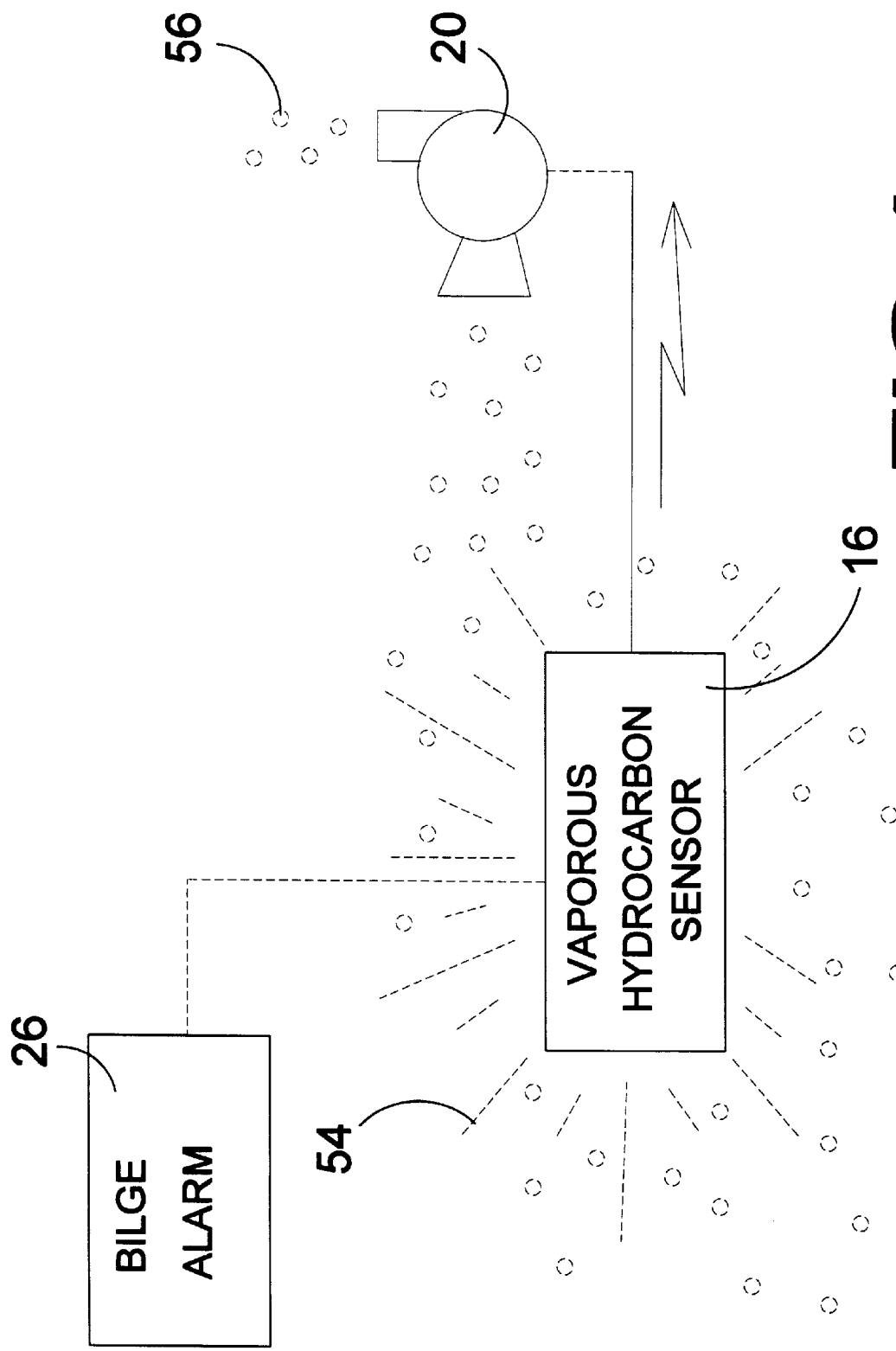
FIG. 4 is a diagrammatic illustration of the present invention as the automatic sensor detects the pollutant and sends a signal to automatic shutdown sensor to shut down the bilge pump. A signal is sent to the bilge sentinel alarming security and alarm arrays.

Turning to FIG. 4, shown therein is a diagrammatic illustration of the present invention as the automatic sensor detects the pollutant vapors 54 and sends a signal to automatic shutdown sensor 16 to shut down the bilge pump. A signal is sent to the bilge sentinel alarming security and alarm arrays 26 engaging blower 20 which exhausts to the atmosphere 56.

Figure 5:
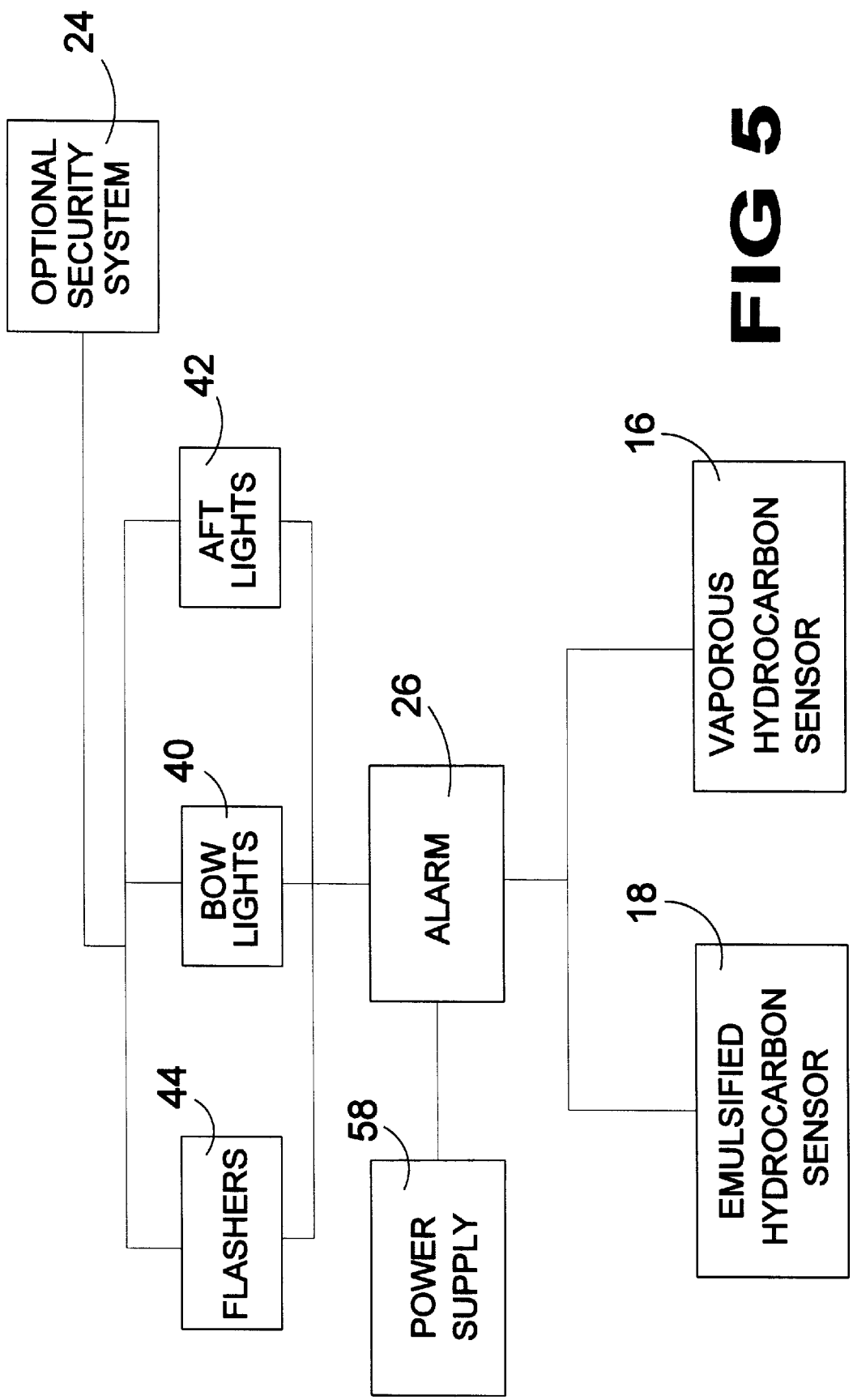
FIG. 5 is a side view of a vessel equipped with the present invention activated due to the presence of hydrocarbons in the bilge. The hydrocarbon sensor has detected pollutants in the bilge and has shut down the bilge pump and activated the blowers, which serve to remove volatile vapors from the bilge area.

Turning to FIG. 5, shown therein is a block diagram of the present invention 10. Elements previously disclosed are shown along with a power supply 58.

Figure 6:
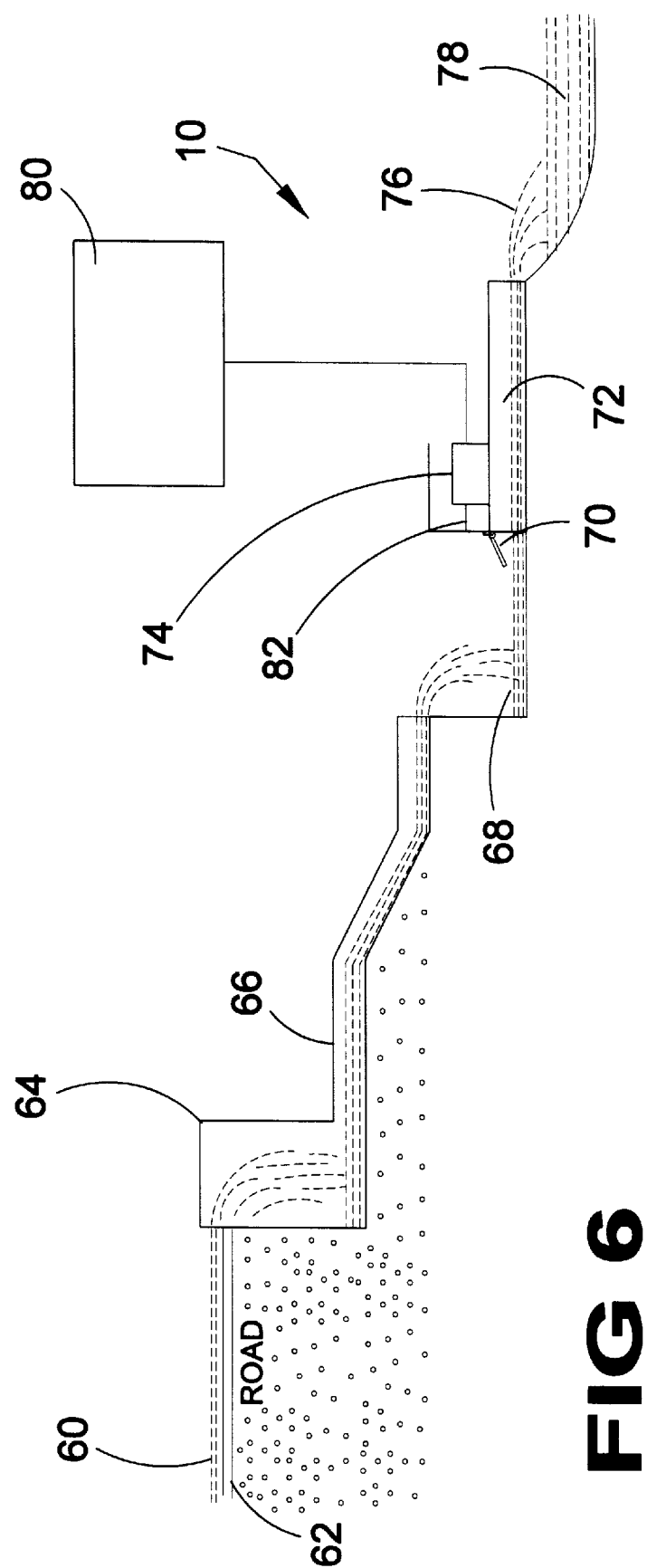
FIG. 6 is a diagrammatic illustration of the present invention installed in a storm drain run-off system under normal operating conditions. Rainwater is running off a roadway and into a storm drain and then funneled into a piped system leading to a holding reservoir where it passes through an open shut-down gate into a discharge pipe where a hydrocarbon sensor monitors for pollutants. The absence of hydrocarbons allows the run-off to continue to discharge freely into the pond or ocean.

Turning to FIG. 6, shown therein is a diagrammatic illustration of the present invention 10 installed in a storm drain run-off system under normal operating conditions. Rainwater runoff 60 is running off a roadway 62 and into a storm drain 64 and then funneled into a piped system 66 leading to a holding reservoir 68 where it passes through an open shut-down gate 70 into a discharge pipe 72 where a hydrocarbon sensor 74 monitors for pollutants. The absence of hydrocarbons allows the run-off to continue to discharge 76 freely into the pond or ocean 78. Storm drain 64 could be sewage treatment runoff or process plant discharge. Also shown are an alarm monitor 80 and shutdown sensor 82.

Figure 7:
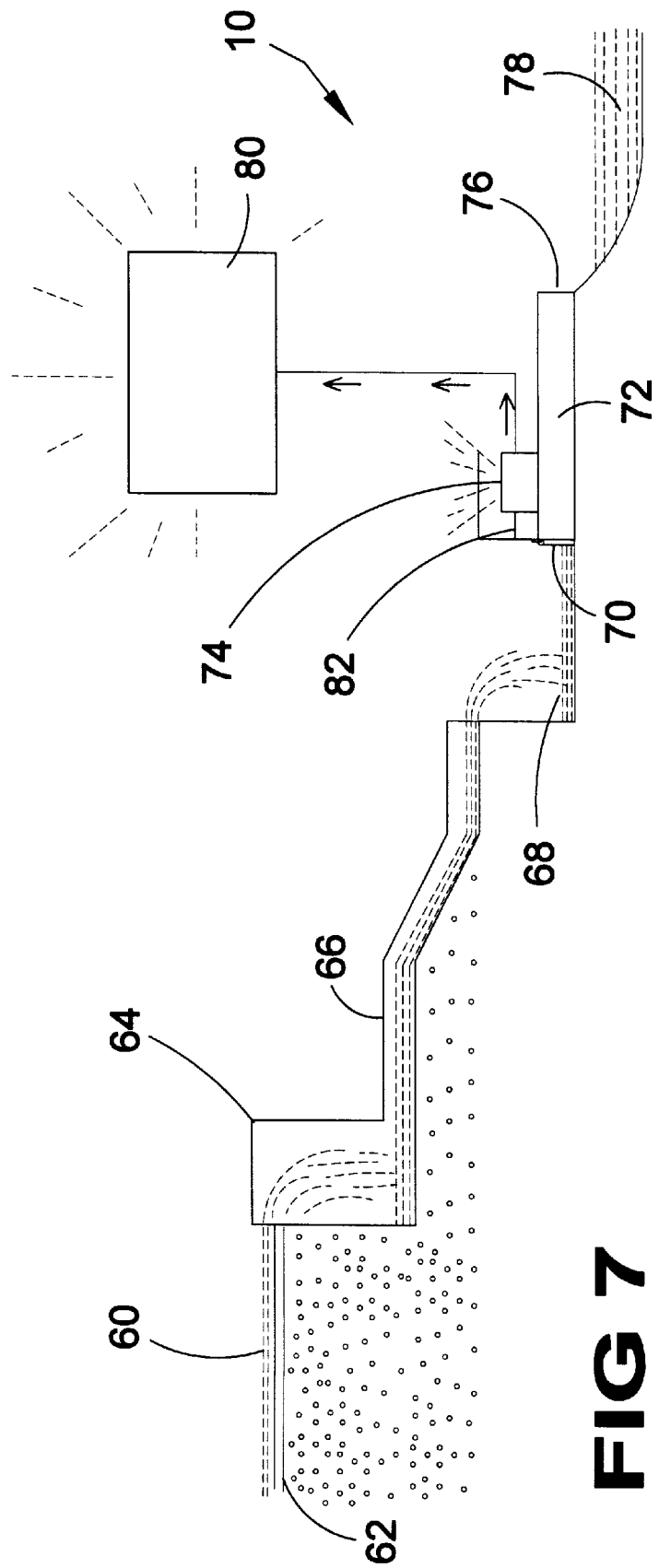
FIG. 7 is a diagrammatic illustration of the present invention installed in a storm drain run-off system during contaminated conditions. Rainwater is running off a roadway and into a storm drain and then funneled into a piped system leading to a holding reservoir where it is contained by the shutdown gate after the hydrocarbon sensor detected pollutants entering the discharge pipe. The run-off is then contained within the holding reservoir or pipe system until pollutants can be properly removed. The activation of the shutdown gate activates an alarm monitor in the central office of the business or agency responsible for maintaining the line to alert them to the environmentally hazardous situation.

Turning to FIG. 7, shown therein is a diagrammatic illustration of the present invention 10 installed in a storm drain run-off system during contaminated conditions. Rainwater runoff or pollutant 60 is running off a roadway 62 and into a storm drain 64 and then funneled into a piped system 66 leading to a holding reservoir 68 where it is contained by the shutdown gate 70 after the hydrocarbon sensor 74 detected pollutants entering the discharge pipe 72. The run-off is then contained within the holding reservoir or pipe system 68 until pollutants can be properly removed by pumping with a vacuum truck. The activation of the shutdown gate 70 activates an alarm monitor 80 in the central office of the business or agency responsible for maintaining the line to alert them to the environmentally hazardous situation. Discharge 76 is eliminated by this system.

What is claimed to be new and desired to be protected by letters patent is set forth in the appended claims:

1. In a vessel having a bilge area, a bilge pump wherein the bilge pump has an intake, a discharge line and a discharge port, a horn, a bow light and an aft light, an engine and an engine ignition system, the improvement comprising:
   a) a vaporous hydrocarbon sensor, said vaporous sensor for detecting the presence of hydrocarbons;
   b) an emulsion hydrocarbon sensor, said emulsion sensor for detecting the presence of hydrocarbons;
   c) means for an alarm whereby said alarm is activated by the presence of vaporous or emulsion hydrocarbons;
   d) means for an exhaust whereby said exhaust is activated by the presence of vaporous hydrocarbons; and,
   e) means for electrically connecting said vaporous hydrocarbon sensor, said emulsion hydrocarbon sensor, said means for an alarm, and said means for an exhaust.

2. The apparatus of claim 1, wherein said vaporous hydrocarbon sensor is disposed at an elevation above the bilge pump.

3. The apparatus of claim 1, wherein said emulsion hydrocarbon sensor is disposed in the bilge pump intake.

4. The apparatus of claim 1, further comprising means for shutting down the bilge pump when said emulsion hydrocarbon sensor detects the presence of hydrocarbons.

5. The apparatus of claim 1, said means for an alarm further comprising a bilge alarm.

6. The apparatus of claim 5, further comprising flashers.

7. The apparatus of claim 5, further comprising bow lights and aft lights.

8. The apparatus of claim 1, further comprising means for shutting off the ignition system when said vaporous hydrocarbon sensor detects the presence of hydrocarbons.

9. In a drain pipe receiving runoff from a source, the pipe having an inlet and an outlet, the improvement comprising:
   a) a gate disposed on the inlet of the pipe, said gate for shutting off flow through the pipe when said gate is closed;
   b) a vaporous hydrocarbon sensor, said vaporous sensor for detecting the presence of hydrocarbons;
   c) an emulsion hydrocarbon sensor, said emulsion sensor for detecting the presence of hydrocarbons;
   d) means for an alarm whereby said alarm is activated by the presence of vaporous or emulsion hydrocarbons; and,
   e) means for electrically connecting said vaporous hydrocarbon sensor, said emulsion hydrocarbon sensor, and said means for an alarm.

10. The apparatus of claim 9, wherein said vaporous hydrocarbon sensor is disposed at an elevation in the pipe above the pipe inlet.

11. The apparatus of claim 9, wherein said emulsion hydrocarbon sensor is disposed in the pipe inlet.

12. The apparatus of claim 9, further comprising a means for a holding reservoir whereby runoff is held when said gate is closed.

13. The apparatus of claim 9, wherein said drain pipe is a storm drain.

14. The apparatus of claim 9, wherein said drain pipe is a sewage treatment effluent discharge pipe.

15. The apparatus of claim 9, wherein said drain pipe is a process plant discharge pipe.

* * * * *